(12) United States Patent
Donnelly et al.

(10) Patent No.: US 6,677,139 B1
(45) Date of Patent: Jan. 13, 2004

(54) METHODS FOR PRODUCTION OF PROTEINS IN HOST CELLS

(75) Inventors: Mark Donnelly, Warrensville, IL (US); Andrzej Joachimiak, Bolingbrook, IL (US)

(73) Assignee: Genecor International, Inc., Rochester, NY (US)

(*) Notice: Subject to any disclaimer, the term of this patent is extended or adjusted under 35 U.S.C. 154(b) by 0 days.

(21) Appl. No.: 09/470,830

(22) Filed: Dec. 23, 1999

(51) Int. Cl.[7] ................. C12N 15/09; C12N 15/00; C12N 1/20; C12P 21/06; C07H 21/04

(52) U.S. Cl. ............. 435/69.7; 435/69.1; 435/320.1; 435/471; 435/252.1; 435/252.3; 435/252.8; 435/325; 435/455; 536/23.1; 536/23.4

(58) Field of Search ................ 536/23.1, 23.4; 435/69.1, 69.7, 320.1, 455, 325, 252.1, 471, 252.3, 252.8

(56) References Cited

U.S. PATENT DOCUMENTS 5,302,518 A    4/1994    Neupert et al.

FOREIGN PATENT DOCUMENTS

| WO | WO 92/05249 | 4/1992 |
| WO | WO 93/13200 | 7/1993 |
| WO | WO 94/08012 | 4/1994 |
| WO | WO 94/23042 | 10/1994 |
| WO | WO 95/31994 | 11/1995 |
| WO | WO 98/56928 | 12/1998 |
| WO | WO 99/31220 | 6/1999 |
| WO | WO 00/66756 | 11/2000 |

OTHER PUBLICATIONS

Dale, et al. Increased Solubility of Trimethoprim–Resistant Type S1 DHFR From Staphylococcus aureas in *Escherichia coli* Cells Overproducing the Chaperonins GroEL and GroES. Protein Engineering, 1994, vol. 7, No. 7, pp. 925–931.*

Ishii, et al. Production of MBP (Maltose Binding Protein)–GroES Fusion Protein and Utilization to Stimulate GroEL–Mediated Protein Refolding. Journal of Fermentation and Bioengineering, 1998, vol. 85, No. 1, pp. 69–73.*

Altamirano et al., "Refolding Chromatography with Immobilized Mini–chaperonins," *Proc. Natl. Acad. Sci. USA*, vol.94, pp. 3576–3578 (Apr. 1997).

Amrein et al., "Purification and characterization of Recombinant Human p50csk Protein–tyrosine Kinase from an *Escherichia coli* Expression System Overproducing the Bacterial Chaperones GroES and GroEL," *Proc. Natl. Acad. Sci. USA*, vol. 92, pp. 1048–1052 (Feb. 1995).

Barbosa et al., "Cloning, sequencing and expression of stress genes from the ethanol–producing bacterium *Zymomonas mobilis*: the grpESL operon," *Gene*, 128 pp. 51–57 (1994).

Brazil, et al., "Model Peptide Studies Demonstrate That Amphipathic Secondary Strufctures Can Be Recognized by the Chaperonin GroEL (cpn60)," *Journal of Biological Chemistry*, vol. 272, No. 8, pp. 5105–5111 (1997).

Buckle et al., "A Structural Model for GroEL–polypeptide recognition," *Proc. Natl. Acad. Sci. USA*, vol. 94, pp. 3571–3575 (Apr. 1996).

Clarke, "Molecular Chaperones in Protein Folding Translocation," *Current Opinion in Structural Biology* 1996, 6:43–50.Buckle et al., "A Structural Model for GroEL–polyeptide recognition," *Proc. Natl. Acad. Sci. USA*, vol. 94, pp. 3571–3575 (Apr. 1996).

Georgiou et al.,"Expression of Correctly Folded Proteins in *Escherichia coli*," *Current Opinion in Structure Biology* 1996, 7:190–197.

Gilbert. "Pseudomonas Lipases: Biochemical Properties and Molecular Cloning," *Enzyme Mocrob. Technol.*, Vol 15, pp. 634–645 (Aug. 1993).

Hartke et al., "Differential Induction of the Chaperonin GroEL and the Co–Chaperonin GrosES by Heat, Acid, and UV–Irradiation in *Lactococcus lactis* subsp. *lactis*," *Current Microbiology*, V. 34 (1997), pp. 23–26.

Hartl et al., "Molecular Chaperones in Cellular Protein Folding," *Current Opinion in Structural Biology* 1995, 5: 92–102.

Hemmingsen, et al., "Homologous plant and bacterial proteins chaperone oligomeric protein assembly," *Nature*, 333: 330–334 (1988).

Hunt, et al., "The Crystal Structure of the GroES Co–chaperonin at 2.8A Resolution," *Nature*, vol. 379, pp. 37–45 (Jan. 1996).

Joerger et al., "Overexpression of a *Thizopus delemar* Lipase Gene in *Escherichia coli*," *LIPIDS*, V. 28, N. 2 pp. 81–88, 1993.

Landry et al., "Interplay of structure and disorder in cochaperonin mobile loops," *Proc. Natl. Acad. Sci. USA*, V. 93, pp. 11622–11627, Oct. 1996.

Landry et al., "Characterization of a functionally important mobile domain of GroES," *Nature*, vol. 364, pp. 255–258 (Jul. 1993).

Landry et al., "Different Conformations for the Same Polypeptide Bound to Chaperones Dnak and GroEL," *Nature*, vol. 355, pp. 455–457 (Jan. 1992).

Mayhew et al., "Protein Folding in the Central Cavity of the GroEL–GroES Chaperonin Complex," *Nature*, vol. 379, pp. 420–426 (Feb. 1996).

(List continued on next page.)

Primary Examiner—Gerald G. Leffers, Jr.
(74) Attorney, Agent, or Firm—Kamrin T. MacKnight (57) ABSTRACT

The present invention provides methods for the production of proteins, particularly toxic proteins, in host cells. The invention provides methods which use a fusion protein comprising a chaperonin binding domain in host cells induced or regulated to have increased levels of chaperonin which binds the chaperonin binding domain.

18 Claims, 3 Drawing Sheets

OTHER PUBLICATIONS

Mullaney et al., GFP:HIV-1 Protease Production and Packaging with a T4 Phage Expression–Packaging Processing System, *Biotechniques,* 1998, Dec.: 25 (6): 1008–12.

Nakanishi et al. "Cloning, Sequencing and Regulation of the Lipase Gene from Pseudomonas," in *Lipases: Structure, Mechanism and Genetic Engineering,* eds. Alberghina et al.

Oltval et al., "Bcl-2 Heterodimerizes in Vivo with a Conserved Homolog, Bax, That Accelerates Programed Cell Death," *Cell,* V. 74, pp. 609–619, Aug. 1993.

Phadtare et al., "Refolding the Release of Tubulins by a Functional Immobilized groEL Column," *Biochimica et Biophysica Acta* 1208, pp. 189–192 (1994).

Rippmann et al., "Procaryotic Expression of Single–Chain Variable–Fragment (scFv) Antibodies: Secretion in L–Form Cells of *Proteus mirabilis* Leads to Active Product and Overcomes the Limitations of Periplasmic Expression in *Escherichia coli,*" *Applied and Environmental Microbiology,* V. 64, N. 12, pp. 4862–4869, Dec. 1998.

Sarkar et al., "Production, Purification, and Characterization of Recombinant 2', 5'–Oligoadenylate Synthetases," *Methods: A Companion to Methods in Enzymology,* vol. 15, 233–242 (1998).

Subrahmanyam et al., Overproduction of a functional fatty acid biosynthetic enzyme blocks fatty acid synthesis in *Escherichia coli,* J. Bacteriol, 1998 Sep.; 180 (17):4596–4602.

Thomas et al., "Protein Misfolding and Inclusion Body Formation in Recombinant *Escherichia coli* Cells Overexpressing Heat–shock Proteins," *The Journal of Biological Chemistry,* V. 271., No. 19, Issue of May 10, pp. 11141–11147, 1996.

Thomas et al., "Divergent Effects of Chaperone Overexpression and Ethanol Supplementation on Inclusion Body Formation in Recombinant *Escherichia coli,*" *Protein Expression and Purification,* V. 11, pp. 289–296 (1997).

Vandier et al., Selective Killing of Glioma Cell Lines Using an Astrocyte–specific Expression of the Herpes Simplex Virus–Thymidine Kinase Gene, *Cancer Research,* V. 58, pp. 4577–4580, Oct. 1998.

Van Dyk, et al., Journal of Bacteriology. vol. 177, No. 20, pp6001–6004, 1995.

Volker et al., "Analysis of the induction of general stress proteins of *Bacillus subtillis,*" *Microbiology,* V. 140, pp. 741–752 (1994).

Welch, William J., "Heat shock proteins functioning as molecular chaperones: their roles in normal and stessed cells," *Phiios Trans R. Soc Lond B. Biol. Sci.,* v. 339 (1289) pp. 327–33 (Mar. 1993).

Xu et al, "The crystal structure of the asymmetric GroEL–GrosES–(ADP)$_7$ chaperonin complex," *Nature,* V. 388, Aug. 1997.

* cited by examiner

GroEL-Binding Loop of GroES Protein of E. coli

Amino Acid Sequence

E  V  E  T  K  S  A  G  G  I  V  L  T  G  S  A  A  A

Corresponding DNA Sequence

GAAGTTGAAACCAAATCTGCTGGTGGTATCGTTCTGACCGGTTCTGCTGCTGCG

FIG._1

Design of a Linker for Attaching the GroEL-Binding Loop of GroES to Proteins

Amino Acid Sequence of GroEL-Binding Loop (Plus Additions | - Met and Asn)

Met Glu Val Glu Thr Lys Ser Ala Gly Gly Ile Val Leu Thr Gly Ser Ala Ala Ala Asn...

Corresponding DNA Sequence and Overhangs for Cloning

AATTATGGAAGTTGAAACCAAATCTGCTGGTGGTATCGTTCTGACCGGTTCTGCTGCG
TACCTTCAACTTTGGTTTAGACGACCACCATAGCAAGACTGGCCAAGACGACGCTTAA

Oligonucleotides Matching the Two Sequences Shown Above Were Synthesized Chemically, Annealed to Generate the Duplex DNA Fragment, and Cloned into Appropriate Vectors. Linkage to a Gene Via the EcoRI Overhang Generates a Protein 20 aa's (1905 Daltons) Longer.

METHODS FOR PRODUCTION OF PROTEINS IN HOST CELLS

FEDERALLY SPONSORED RESEARCH OR DEVELOPMENT

This invention was made with Government support under Grant No. 70NANB5H1138 awarded by Advanced Technology Program/National Institute of Standards and Technology. The Government has certain rights in this invention.

This Invention was made with Government support under ANL Work-for-Others Proposal No. P-95090; Prime Contract W-31-198-ENG-38 awarded by the Department of Energy. The Government has certain rights In this Invention.

FIELD OF THE INVENTION

The present invention generally relates to methods for the production of proteins in host cells. Specifically, the present invention relates to the use of a chaperonin binding domain in expression systems designed for the production of proteins in host cells.

BACKGROUND OF THE INVENTION

One of the simplest and most inexpensive ways to obtain large quantities of desired polypeptides for commercial or research uses is through the expression of heterologous genes in bacterial cells. Often however, net accumulation of the recombinant polypeptide is low due to degradation, missfoldings or aggregation. Also, many recombinant polypeptides fail to attain their correct three-dimensional conformation in *E.coli* and are found sequestered within large refractile aggregates, i.e., inclusion bodies. Processes for recovering active polypeptides from inclusion bodies can be complex and expensive. Additionally, in some cases, the large scale production of a protein is limited by the toxicity of the overexpressed protein toward the host cell or the accumulation of proteins as inclusion bodies that impede their recovery and purification.

In the cell, a class of accessory proteins known as molecular chaperones function by interacting with nascent polypeptide chains and aid in the process of correct folding Georgiou et al. (1996, Current Opinion in Biotechnology, 7:190–197). Molecular chaperones are highly conserved proteins found in all organisms that control and sometimes catalyse the ATP-dependent folding of newly synthesized proteins and polypeptides as they are produced in cells. Chaperones mediate the stabilization and refolding of proteins under conditions of stress and are believed to fold crucial portions of proteins, such as enzymes, independently (Hendrick, J. P., 1993, *Ann. Rev. Biochem.* 62: 349–384).

Several *E.coli* proteins have been shown to exhibit chaperone activity: the 60 kDa heat shock protein (Hsp60) GroEL, a chaperonin and the smaller accessory protein GroES (10 kDa); the DnaK (Hsp70), DnaJ and GrpE complex; and the Clp system. Georgiou et al. supra. GroEL consists of 14 subunits which are arranged in two heptameric rings stacked back to back. The central cavity of the cylinder accepts unfolded substrate polypeptides in the conformation of a collapsed intermediate. GroEL interacts with GroES, a single heptameric ring that binds asymetrically to GroEL, capping one opening of the cylinder. GroES coordinates the ATP hydrolysis by GroEL with productive folding (Mayhew, M et al., *Nature* vol. 379:420–426.)

Dale, G. et al. (1994, Protein Engineering 7:925–931) report that simultaneous overproduction of the GroEL/GroES chaperonins with dihydrofolate reductase results in an increased solubility of the enzyme and Amrein, K. et al. (1995, Proc. Natl. Acad. Sci. vol 92: 1048–1052) report on the purification of recombinant human protein-tyrosine kinase in an *E.coli* expression system overproducing the bacterial chaperonins GroES and GroEL.

Landry, S. et al. (1993, Nature 364:255–258) disclose a polypeptide loop of the GroES/GroEL complex and Altamirano et al. (1997, Proc. Natl. Acad. Sci. USA, 94:3576–3578) disclose the use of immobilized fragments of the GroEL chaperonin in chromatography.

In spite of advances in understanding chaperonins and the production of proteins in host cells, there remains a need to develop expression vectors and systems which allow for production of proteins in host cells.

SUMMARY OF THE INVENTION

The present invention generally relates to chaperonin protein binding domains and to the use of an isolated chaperonin protein binding domain in the production of heterologous proteins, peptides or polypeptides in a host cell. The present invention is based, in part, upon the finding that a toxic gene product could be recombinantly produced by a host cell when expressed as a fusion protein associated with an isolated chaperonin binding domain.

Accordingly, the present invention provides a method for producing a protein in a host cell, comprising the step of culturing a host cell comprising a first nucleic acid encoding an isolated chaperonin binding domain associated with a second nucleic acid encoding the protein and a third nucleic acid encoding a chaperonin under conditions suitable for expression of said first, said second and said third nucleic acid and wherein said chaperonin binding domain is capable of binding to said chaperonin. In a further embodiment, the chaperonin binding domain and the chaperonin are capable of binding with an affinity of between about $10^{-2}$ and $10^{-8}$ Kd. The method may further comprise recovering said protein from said cell. In one aspect, the protein is one toxic to the host cell. A protein may be toxic to a host cell due to its intrinsic nature or toxic due to the presence of elevated levels in the host cell.

In another embodiment of the present invention, the first and second nucleic acid encode a fusion protein. The first and second nucleic acid may be directly linked or indirectly linked by nucleic acid encoding an enzymatic cleavage site, a chemical cleavage site, or another protein or peptide.

In one aspect of the invention, nucleic acid encoding the chaperonin is naturally produced by the host cell and the cell is grown under conditions that result in elevated levels of the chaperonin. In another aspect, nucleic acid encoding the chaperonin is heterologous to the host cell and the heterologous chaperonin is under the control of at least one expression signal capable of overexpressing the chaperonin in the host cell. The present invention encompasses any host cell that is capable of expression of recombinant proteins. In one embodiment, the host cell is a bacterium. In another embodiment, the host cell is a eubacterium. In yet further embodiments, the host cell is a gram-positive or a gram-negative bacterium. In a further embodiment, the bacterial cell is a member of the family Enterobacteriaceae. In an additional embodiment, the bacterial cell is an Escherichia species, in particular *E. coli*.

There are several well characterized chaperonin systems known in the art having two or more interacting partners, for example, Hsp60 and Hsp10 (GroEL/GroES); Hsp70 and Hsp40 and GrpE (DnaK/DNAJ/GrpE); ClipA/X and ClipP; Hsp90 and Hsp70 and other factors; TriC and other factors.

The present invention encompasses chaperonin binding domains obtainable from these systems as long as the chaperonin binding domain is capable of binding to a chaperonin with an affinity of between about $10^{-2}$ and $10^{-8}$ Kd. In one embodiment, the chaperonin binding domain has the sequence as shown in SEQ ID NO: 3 through SEQ ID NO: 40. In yet another embodiment, the chaperonin binding domain is obtainable from the GroES co-chaperonin and said chaperonin is the GroEL chaperonin. In another embodiment, the binding domain comprises the amino acid sequence EVETKSAGGIVLTGSAAA(SEQ ID NO:2), In a further embodiment, the binding domain comprises a variation of the sequence EVETKSAGGIVLTGSAAA(SEQ ID NO:2), said variant being capable of binding to GroEL chaperonin with an affinity of $10^{-2}$ to $10^{-8}$ Kd. The present invention also provides expression vectors and host cells comprising a chaperonin protein binding domain.

Examples of heterologous proteins include therapeutically significant proteins, such as growth factors, cytokines, ligands, receptors and inhibitors, as well as vaccines and antibodies; enzymes such as hydrolases including proteases, carbohydrases, and lipases; isomerases such as racemases, epimerases, tautomerases, or mutases; transferases, kinases and phophatases; and commercially important industrial proteins or polypeptides, such as proteases, carbohydrases such as amylases and glucoamylases, cellulases, oxidases and lipases. The nucleic acid encoding the heterologous protein may be naturally occurring, a variation of a naturally occurring protein or synthetic.

DETAILED DESCRIPTION OF PREFERRED EMBODIMENTS

Definitions

The in vivo cellular processes of protein folding and assembly are controlled by molecular mechanisms associated with molecular chaperones such as chaperonins. As used herein, the term "chaperonin" refers to those molecules including heat shock proteins Hsp60 and like proteins that are expressed in any organism which are associated with protein folding. The present invention encompasses any chaperonin from any microbial source, virus or bacteriophage including the chaperonin systems, Hsp60 and Hsp10 (GroEL/GroES); Hsp70 and Hsp40 and GrpE (DnaK/DNAJ/GrpE); ClipA/X and ClipP; Hsp90 and Hsp70; and TriC. In a preferred embodiment, the chaperonin binding domain and the chaperonin are obtainable from the heat shock protein 60 (HSP60) class of proteins. Other chaperonins include mammalian or yeast HSP68, HSP70, HSP72, HSP73, clathrin uncoating ATPase, IpG heavy chain binding protein (BiP), glucose-regulated proteins 75, 78, and 80 (GRP75, GRP78, and GRP80), HSC70, and yeast KAR2, BiP, SSA1–4, SSB1, SSD1 and the like. Chaperone proteins which can increase protein secretion also include enzymes which catalyze covalent modification of proteins, such as mammalian or yeast protein disulfide isomerase (PDI), prolyl-4-hydroxylase B-subunit, ER p59, glycosylation site binding protein (GSBP) and thyroid hormone binding protein (T3BP).

Chaperonins are known to be associated with protein folding and anti-aggregation activities (Craig, et al., 1994, Cell vol. 78, 365–372; Hendrick, et al., 1993, Annu. Rev. Biochem. Vol.62, 349–84; Hartl, 1994, TIBS vol.19:20–25). Often, multiple sub-units are associated with one chaperonin complex. The present invention encompasses each chaperonin sub-unit used individually or in combination with other subunits providing that the individual subunit or combination of subunits is able to function by binding to a chaperonin protein binding domain. In the present invention, preferred chaperonins are those present in members of the family Enterobacteriaceae and in particular from Eschericia species. In the present invention, a preferred chaperonin is the GroEL chaperonin which is associated with the co-chaperonin GroES. A chaperonin of the present invention may be naturally occurring in the host cell or heterologous to the host cell and may be introduced by recombinant means.

Figure 1:
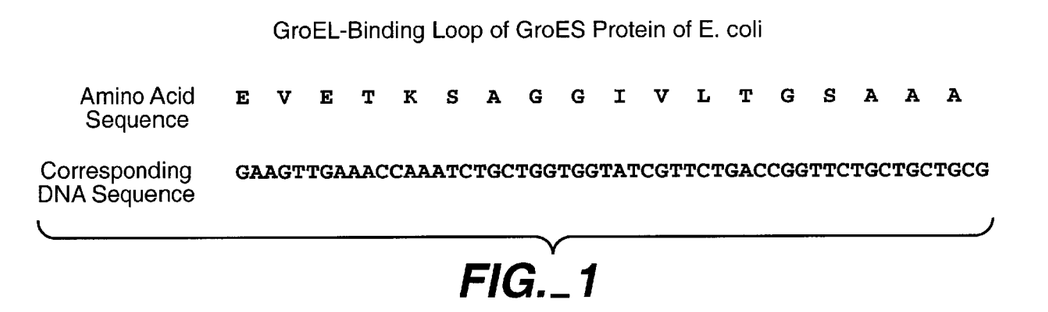
FIG. 1 shows the nucleic acid (SEQ ID NO:1) and amino acid (SEQ ID NO:2) for the region of the chaperonin containing the GroEL/GroES binding domain.

As used herein, the phrase "isolated binding domain" of a chaperonin or "chaperonin protein binding domain" or "chaperonin binding domain" refers to a region of a protein or polypeptide that is able to bind with an affinity of between $10^{-2}$ and $10^{-8}$ Kd to a chaperonin or portion or fragment thereof of said chaperonin. In one embodiment of the present invention, the chaperonin binding domain has the sequence as shown in any of SEQ ID NO:3 through SEQ ID NO:40. In another embodiment of the present invention, the chaperonin binding domain is obtainable from the GroES co-chaperonin. As used herein, the chaperonin protein binding domain obtainable from GroES refers to the residues shown in FIG. 1 comprising the sequence EVETKSAGGIVLTGSAAA(SEQ ID NO:2). In another embodiment, the binding domain comprises amino acid variations of EVETKSAGGIVLTGSAAA(SEQ ID NO:2) capable of binding to a GroEL chaperonin with an affinity of between $10^{-2}$ and $10^{-8}$ Kd. A chaperonin protein binding domain is associated with a second nucleic acid encoding a heterologous protein when the first and second nucleic acids are directed linked, such as in a fusion protein, or are indirectly linked such as having an enzymatic cleavage site, chemical cleavage site or other nucleic acid inserted between the first and the second nucleic acid.

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand. As used herein "amino acid" refers to peptide or protein sequences or portions thereof.

The terms "isolated" or "purified" as used herein refer to a nucleic acid or amino acid that is removed from at least one component with which it is naturally associated.

As used herein, the term "heterologous protein" refers to a protein or polypeptide that is encoded by nucleic acid introduced into a host cell. Examples of heterologous proteins include enzymes such as hydrolases including proteases, carbohydrases, and lipases; isomerases such as racemases, epimerases, tautomerases, or mutases; transferases, kinases and phophatases. The heterologous gene may encode therapeutically significant proteins or peptides, such as growth factors, cytokines, ligands, receptors and inhibitors, as well as vaccines and antibodies. The gene may encode commercially important industrial proteins or peptides, such as proteases, carbohydrases such as amylases and glucoamylases, cellulases, oxidases and lipases. The gene of interest may be a naturally occurring gene, a mutated gene or a synthetic gene. The term "homologous protein" refers to a protein or polypeptide that naturally occurs in the host cell. The present invention encompasses homologous proteins that are introduced into the host cell via recombinant means. The term "toxic" as used herein refers to any protein that inhibits the growth of a bacterial cell. A protein may be toxic to a host cell due to an intrinsic harmful nature or due to expression levels in the host bacterial cell. An illustrative example of a toxic protein disclosed herein is the mouse apoptosis modulator protein, Bax. Examples of proteins considered to be toxic due to their intrinsic nature include nucleases, proteases and phospholipases.

As used herein, the term "overexpressing" when referring to the production of a protein in a host cell means that the protein is produced in greater amounts than it is produced in its naturally occurring environment.

DETAILED DESCRIPTION OF THE PREFERRED EMBODIMENTS

The present invention provides a means for the production of proteins or polypeptides in a host cell, especially proteins or polypeptides that are toxic to the cell due to the protein's intrinsic nature or due to expression levels of the protein produced recombinantly in the cell.

The present invention provides methods for producing a protein in a host cell wherein the cell comprises nucleic acid encoding a fusion protein comprising a chaperonin binding domain and the protein and wherein the cell naturally produces a chaperonin that binds to the chaperonin binding domain. In this embodiment, the host cell is grown under conditions suitable for inducing or enhancing the levels of the naturally occurring chaperonin. The present invention encompasses methods for producing a protein in a host cell wherein the cell comprises nucleic acid encoding a fusion protein comprising a chaperonin binding domain and protein and said host cell further comprises nucleic acid encoding a chaperonin that has been recombinantly introduced into said host cell. In this embodiment, the chaperonin may be homologous or heterologous to said host cell and is associated with expression signals capable of overexpressing the chaperonin.

In an illustrative example disclosed herein, the mammalian gene bax, a member of the bcl-2 family of apoptosis modulators (Oltvai, Z. N., Milliman, C. L., and Korsmeyer, S. J. (1993) Bcl-2 Heterodimerizes in vivo with a conserved Homolog, Bax, that accelerates Programmed cell death, Cell 74, 609–619) was used. Although homologous to bcl-2 and bcl-$X_L$, which inhibit apoptosis, bax has the opposite function and is an effector of cell death (McDonnell, T. J., et al., 1996, Importance of the Bcl-2 family in cell death regulation, Experientia 52, 1008–1017). These three genes were expressed in *E. coli* as fusions with the OmpA leader sequence. Bcl-2 and Bcl-$X_L$ proteins were produced in the periplasm of *E. coli*, but only trace amounts of Bax was produced by this approach. Expression of Bax appeared to be highly toxic to the host cell. No expression of the native form of Bax was observed from any clones when we placed the bax cDNA sequence adjacent to the lac promoter. When the bax gene was linked to a chaperonin binding domain obtainable from GroES and produced as a fusion protein in *E.coli* simultaneous with overproduction of the GroEL chaperonin, overexpression of the Bax protein was observed, suggesting that the toxic effect of Bax on the host cell had been reduced.

I. Chaperonin Nucleic Acid and Amino Acid Sequences

The present invention encompasses chaperonin proteins that are associated with increased protein secretion and those that are associated with the folding and unfolding of polypeptides, including but not limited to, the heat shock 60 family of proteins (Hsp60).

In one embodiment, the chaperonin is obtained from an organism listed in Table I and has the respective chaperonin binding domain as given in Table I. In a preferred embodiment herein, the chaperonin is GroEL the nucleic acid and amino acid sequence of which is disclosed in Hemmingsen, et al., 1988, Nature vol. 333, pages 330–334. A method for isolation of GroEL is described, for example, in the reference Hendrix, R. W. 1979, J. Mol. Biol. 129:375–392.

The chaperonin may be naturally occurring in the host cell in which case the host cell comprising the chaperonin is subjected to conditions that result in an increase in the production of the chaperonin. This provides elevated levels of chaperonin to which the chaperonin binding domain attaches. Methods for inducing the natural levels of chaperonin in a host cell include heat shock (Welch W. J., 1993, Philos Trans R. soc Lond B Biol Sci vol. 339, pages 327–333); chemical shock, such as by the addition of ethanol, methanol, glucose, and drugs such as those described in Volker et al., 1994, Microbiology, vol 140: pages 741–752; Barbosa et al., Gene, 1994, vol. 148, pages 51–57; and Hartke, 1997, Curr Microbiol, vol 34, pages 23–26.

The chaperonin may be heterologous to the cell and introduced into the cell via recombinant means. The heterologous chaperonin, or portions or fragments thereof capable of binding to the chaperonin binding domain, may be introduced via a replicating plasmid or integrated into the host genome by means known to those of skill in the art. The present invention also encompasses host cells having additional copies of homologous chaperoning, or portions or fragments thereof capable of binding to a chaperonin binding domain, introduced into the cell.

In one illustrative example disclosed herein, the host cell used was *E.coli* which naturally produced the GroEL chaperonin as well as the GroES co-chaperonin, and further comprised nucleic acid encoding a fusion of the chaperonin binding domain having the amino acid sequence EVETKSAGGIVLTGSAAA(SEQ ID NO:2) with the mouse apoptosis modulator protein, Bax. The recombinant *E.coli* was subjected to growth conditions that stimulated overproduction of the naturally occurring GroEL chaperonin and expression of the fusion protein was observed.

II. Chaperonin Binding Domain

The present invention encompasses chaperonin binding domains that are capable of binding to a chaperonin with an affinity of between $10^{-2}$ and $10^{-8}$ Kd. Examples of chaperonin binding domains are provided in Table I. Table I provides the sequence of chaperonin binding domains and a list of the respective microorganism from which the binding domain is obtained (Hunt et al., 1996, Nature vol. 379, pages 37–45).

TABLE I

| Organism | Chaperonin binding domain | |
| --- | --- | --- |
| ch10_ecoli | EVETKSAGGIVLTGSAAAK | SEQ ID NO:3 |
| ch10_acype | EVESKSAGGIVLTGSAAGK | SEQ ID NO:4 |
| ch10_haedu | EVETCSAGGIVLTGSATVK | SEQ ID NO:5 |
| ch10_pseae | EEETKTAGGIVLPGSAAEK | SEQ ID NO:6 |
| ch10_chrvi | EEERLSAGGIVIPDSATEK | SEQ ID NO:7 |
| cg10_coxbu | EEERTSAGGIVIPDSAAEK | SEQ ID NO:8 |
| ch10_legmi | EEERTTAGGIVIPDSATEK | SEQ ID NO:9 |
| ch13_rhime | ESEEKTKGGIIIPDTAKEK | SEQ ID NO:10 |
| ch10_legpn | EEERTTAGGIVIPDSATEK | SEQ ID NO:11 |
| ch10_bruab | ESEAKTAGGIIIPDTAKEK | SEQ ID NO:12 |
| ch12_braja | DAEEKTAGGIIIPDTVKEK | SEQ ID NO:13 |
| ch10_agrtu | ESEAKTKGGIIIPDTAKEK | SEQ ID NO:14 |
| ch10_cloab | EAEETTKSGIVLPSSAKEK | SEQ ID NO:15 |
| ch10_amops | EEERTTAGWIVIPDSATEK | SEQ ID NO:16 |
| ch11_rhime | ESEEKTKGGIIIPDTAKEK | SEQ ID NO:17 |
| ch10_lacla | EEEEKSMGGIVLTSASQEK | SEQ ID NO:18 |
| ch10_stral | DAEQTTASGLVIPDTAKEK | SEQ ID NO:19 |
| ch10_thep3 | ETEEKTASGIVLPDTAKEK | SEQ ID NO:20 |
| ch10_bacsu | ESEEKTASGIVLPDSAKEK | SEQ ID NO:21 |
| ch10_bacst | ETEEKTASGLVLPDTAKEK | SEQ ID NO:22 |
| ch10_myctu | EAETTTASGLVIPDTAKEK | SEQ ID NO:23 |
| ch13_braja | DAEEKTAGGIIIPDTAKEK | SEQ ID NO:24 |
| ch10_staau | EQEQTTKSGIVLTDSAKEK | SEQ ID NO:25 |
| ch10_mycbo | EAETTTASGLVIPDTAKEK | SEQ ID NO:26 |
| ch10_mycle | EAETMTPSGLVIPENAKEK | SEQ ID NO:27 |
| ch10_clope | EAEETTKSGIIVTGTAKER | SEQ ID NO:28 |
| ch10_synp7 | EAEEKTAGGIILPDNAKEK | SEQ ID NO:29 |
| ch10_synp6 | EAEEKTAGGIILPDNAKEK | SEQ ID NO:30 |
| ch10_syny3 | PAEEKTAGGILLPDNAKEK | SEQ ID NO:31 |
| ch10_chlpn | EEEATARGGIILPDTAKKK | SEQ ID NO:32 |
| ch10_lepin | QEAEEKIGSIFVPDTAKEK | SEQ ID NO:33 |
| ch10_chlps | EEDSTARGGIILPDTAKKK | SEQ ID NO:34 |
| ch10_chltr | EEASTARGGIILPDTAKKK | SEQ ID NO:35 |
| ch10_rat | AAETVTKGGIMLPEKSQGK | SEQ ID NO:36 |
| ch10_bovin | AAETVTKGGIMLPEKSQGK | SEQ ID NO:37 |
| ch10_ricts | QNDE.AHGKILIPDTAKEK | SEQ ID NO:38 |
| ch10_spiol | EVENKTSGGLLLAESSKEK | SEQ ID NO:39 |
| ch10_arath | IQPAKTESGILLP.EKSSK | SEQ ID NO:40 |

In a preferred embodiment, the chaperonin binding domain is the sequence EVETKSAGGIVLTGSAAA(SEQ ID NO:3) or portions or variations thereof which bind to the GroEL chaperonin with an affinity of between about $10^{-2}$ to about $10^{-8}$ Kd.

For construction of a fusion protein, the chaperonin binding domain may be directly linked to the desired protein, peptide or polypeptide, or indirectly linked, ie comprising additional nucleic acid between the nucleic acid encoding the chaperonin binding domain and the protein or peptide or polypeptide. Such additional nucleic acid may encode enzymatic cleavage sites or chemical cleavage sites. Nucleic acid encoding the chaperonin may be 5' or 3' to the nucleic acid encoding the protein, peptide or polypeptide.

III. Expression Systems

The present invention encompasses expression vectors and host cells comprising a chaperonin binding domain for the production of proteins, peptides or polypeptides in host cells. Nucleic acid encoding a chaperonin binding domain can be isolated from a naturally occurring source or chemically synthesized as can nucleic acid encoding a desired protein, peptide or polypeptide. Once nucleic acid encoding a binding domain of the present invention, or a protein, peptide or polypeptide, is obtained, fusion proteins comprising the chaperonin binding domain and the protein, peptide or polypeptide and recombinant host cells comprising the fusion proteins may be constructed using techniques well known in the art. Molecular biology techniques are disclosed in Sambrook et al., Molecular Biology Cloning: A Laboratory Manual, Second Edition (1989) Cold Spring Harbor Laboratory Press, Cold Spring Harbor, N.Y. (1989). Nucleic acid encoding a chaperonin binding domain and/or protein is obtained and transformed into a host cell using appropriate vectors. A variety of vectors and transformation and expression cassettes suitable for the cloning, transformation and expression in host cells are known by those of skill in the art.

Typically, the vector or cassette contains sequences directing transcription and translation of the nucleic acid, a selectable marker, and sequences allowing autonomous replication or chromosomal integration. Suitable vectors comprise a region 5' of the gene which harbors transcriptional initiation controls and a region 3' of the DNA fragment which controls transcriptional termination. These control regions may be derived from genes homologous or heterologous to the host as long as the control region selected is able to function in the host cell.

Initiation control regions or promoters, which are useful to drive expression of the chaperonin binding domain, or fusion protein comprising the chaperonin binding domain, in a host cell are known to those skilled in the art. Virtually any promoter capable of driving expression is suitable for the present invention. Nucleic acid encoding the chaperonin binding domain is linked operably through initiation codons to selected expression control regions for effective expression of the chaperonin binding domain.

Once suitable cassettes are constructed they are used to transform the host cell. General transformation procedures are taught in Current Protocols In Molecular Biology (vol. 1, edited by Ausubel et al., John Wiley & Sons, Inc. 1987, Chapter 9) and include calcium phosphate methods, transformation using PEG and electroporation.

A host cell which contains the coding sequence for a chaperonin or chaperonin binding domain of the present invention and expresses the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

A host cell comprising a fusion protein comprising a chaperonin binding domain is used to express proteins, peptides or polypeptides which are normally toxic to the host cell. A toxic protein may affect the growth of the cell due to its intrinsic qualities or due to the affects on the cell due to overexpression.

The manner and method of carrying out the present invention may be more fully understood by those of skill in the art by reference to the following examples, which examples are not intended in any manner to limit the scope of the present invention or of the claims directed thereto.

EXAMPLES

Materials and Methods

Genes, strains, media and growth conditions.

*E. coli* strain JM83 was obtained from Dr. Deborah Hanson, Argonne National Laboratory and strain JM105 was from Pharmacia. For cloning, strains were cultured on LB or 2xYT medium with 100 μg/ml ampicillin where appropriate, and for physiological studies, strains were grown on LB medium supplemented with appropriate carbon sources and electron acceptors. The plasmid pASK40 was from Skerra et al., 1991, Bio/Technology 9:273–278, pJF118EH was from Dr. Michael Bagdasarian (Furste et al., 1986, Gene 48, 119–31), pTRC99a and pUC19 were from Pharmacia. Reagents used in polymerase chain reactions (PCR) were from Perkin-Elmer; isopropyl-b-D-thiogalactopyranoside (IPTG) was from US Biochemicals; enzymes for molecular biology were from Promega, Inc.; all other chemicals were purchased from Sigma (St. Louis).

The pSK-mBax plasmid containing the cDNA encoding murine-Bax was a gift from Dr. John C. Reed from the La Jolla Cancer Foundation. The plasmid containing murine-Bcl-2 cDNA was provided by Dr. Timothy J. McDonnell at the University of Texas M. D. Anderson Cancer Center. Nucleic acid sequences for murine bax and murine bcl-2 found in GenBank entries L22472 (Oltvai et al., 1993, Cell, 74:609–619) and M16506 (Negrini et al., 1987, Cell, 49:455–463) were used to design PCR primers that would 1) introduce an EcoRI site at the 5'-end of the gene to allow cloning into the vector pASK40 in the correct reading frame, and 2) encode an additional five histidine residues at the 3'-end of the gene to facilitate purification of expressed proteins (Hochuli et al., 1988, Bio/Technology 6:1321–1325). MDH was previously cloned from genomic E. coli DNA by PCR into pASK40 and pTRC99a (Boemke, et al (1995) Arch. Biochem. Biophys. 322:43–52).

TABLE 2

Plasmids used.

| Plamsid | Components | Source and/or reference |
|---|---|---|
| pASK40 | bla, laclq, P/Olac, t lpp, f1-lG, ompA | (Skerra et al., supra) |
| pJF118EH | bla, laclq, Ptac | (Furste et al., supra) |
| pATP004 | GroES-loop encoding leader in pJF118EH | this application |
| pATP005 | Multicloning site of pUC19 substituted for that of JF118EH in pATP004 | this application |
| pMDH1 | E. coli mdh in pASK40 | (Boernke et al., supra) |
| pMDH13 | E. coli mdh in pTRC99a | (Boernke et al., supra) |
| pATP007 | E. coli mdh in pATP004 | this application |
| pWS213 | BCL-2 in pASK40 | this application |
| pATP010 | BCL-2 in pATP005 | this application |
| pBAX002 | BAX in Xbal/Sal I sites of pASK40 (no leader sequence) | this application |
| pBAX001 | BAX in EcoRI/Sal I sites of pASK40 (ompA leader sequence) | this application |
| pATP011 | BAX from pBAX001 in pATP005 (GroES-loop leader sequence) | this application |

Construction of Vectors for Expressing Chaperonin Binding Domain Fusion Proteins Vectors designed to comprise the chaperonin binding domain obtainable from GroES were constructed as follows. Oligonucleotides were synthesized based on the published amino acid sequence of the E. coli GroES protein. Residues 16 through 33 comprise the chaperonin binding domain EVETKSAGGIVLTGSAAA(SEQ ID NO:2). A nucleotide sequence encoding this sequence and its complement were generated by the program Lasergene (DNAStar, Inc., Madison, Wis.) using the general codon preferences for E. coli. A linker was designed to require the same reading frame as that required in pASK40. Additional nucleotides encoding the overhang generated by an EcoRI digest of DNA and an ATG initiation codon were included at the 5'-end of each to give:

Oligo ATP6: 5'-AATTATGGAAGTTGAAA
CCAAATGTGCTGGTGGTATCG-
TTCTGACCGGTTCTGCTGCTGCG-3'(SEQ ID NO:44)

Oligo ATP7: 5'-AATTCGCAGCAGCAG
AACCGGTCAGAACGATACCACCA-
GCAGATTTGGTTTCAACTTCCAT-3'(SEQ ID NO:42)

Figure 5:
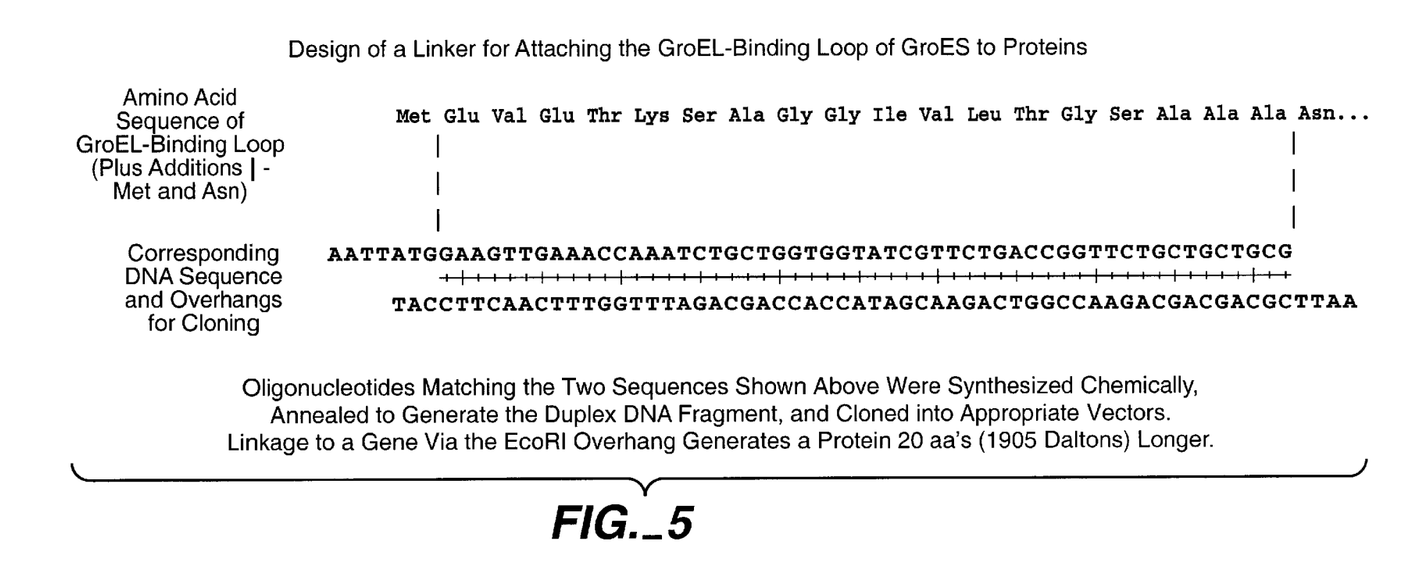
FIG. 5 shows the design of a linker for attaching the GroEL-binding loop of GroES to proteins. Oligonucleotides (SEQ ID NOS:44 and 42) matching the two sequences are shown above were synthesized chemically, annealed to generate the duplex DNA fragment, and cloned into appropriate vectors. Linkage to a gene via the EcoRI overhang generates a protein that is 20 (1905) Daltons longer. The amino acid sequence provided in this Figure corresponds to SEQ ID NO:43.

The design of the linker for attachment of the GroEL-binding domain of GroES to proteins is shown in FIG. 5(SEQ ID NO:43).

The linker was phosphorylated using T4 polynucleotide kinase, purified with Qiaex resin (Qiagen), and ligated into the dephosphorylated EcoRI site of the vector pJF118EH. Transductants of strain JM105 were screened for the presence of an EcoRI site, which is present in the linker but absent in pJF118EH. Positive transductants were screened for orientation of the insert. Only one end regenerates an EcoRI site, and in the correct orientation that site is adjacent to a multicloning site. EcoRI-EcoRV digests were analyzed on a 1.5% agarose gel for the presence of the 1,260 base pair fragment predicted for the correct orientation as opposed to the 1,200 base pair fragment predicted for the reverse orientation. The new vector was designated pATP004.

Because the multi-cloning site of pATP004 was limited in the number of sites available for cloning, we exchanged this cluster for the larger cluster of pUC19 using the enzymes EcoRI and HindIII. Plasmids obtained from JM105 transductants were screened for orientation, as above, and for the presence of the Kpnl and Xbal sites present only in the pUC19 multicloning site. The resulting plasmid was designated pATP005.

Expression and Analysis of Proteins

Cultures containing plasmids were grown in LB medium to $A_{600}$ 0.2–0.5 then induced with 0.1 mM IPTG. To prepare cytoplasmic fractions of total proteins, cells were lysed by treatment with lysozyme. Expression of noncatalytic proteins was estimated by conventional gel electrophoresis. Gels were scanned with a UMax PowerlookII scanner and the images were analyzed with Digital Science 1D software (Eastman Kodak). For more rigorous quantitation, 2-dimensional gel electrophoresis was performed.

Two-dimensional Gel Electrophoresis

Cell pellets (7.85 $OD_{600}$ units) were lysed in 1 mL of a solution containing 9 M urea, 2% 2-mercaptoethanol, 4% Nonidet P40, and 2% ampholytes (BioRad pH 8–10). The resulting homogenates were centrifuged for 5 min at 435×g in a Beckman TL100 tabletop ultracentrifuge to remove particulates. The supernatants were then frozen at −70° C. until electrophoresis. Isoelectric focusing in the first dimension was done essentially as described by Anderson and Anderson (1978, Anal. Biochem, vol. 85, pages 33–340) using 50% pH 3–10 Biolyte, 25% pH 5–7 Biolyte, and 25% pH 5–7 Servalyte carrier ampholytes. After equilibration in sodium dodecyl sulphate buffer (O'Farrell, 1975, J. Bio. Chem., vol. 250, pages 4007–4021) the focused proteins were separated in the second dimension in slab gels containing a linear gradient of 10–17% polyacrylamide, essentially as described by O'Farrell, supra, with modifications described by Anderson and Anderson, 1978, Anal. Biochem, vol. 85: pages 341–354. After electrophoresis, gels were fixed and stained in 0.125% (w/v) Coomassie Blue R250 in 2.5% phosphoric acid and 50% ethanol for approximately 24 h. The gels were then destained in 20% ethanol. Protein patterns were digitized using an Eikonix 1412 CCD scanner interfaced with a VAXstation 4000-90. Image processing and generation of parameter lists, referred to as spot files, were as previously described Anderson, 1982. A master pattern was created using a copy of a 2DE spot file from the "ethanol and induced" treatment group so that the Bax protein was represented. Each of the patterns generated for the experiment, with four replicate patterns within each sample group, was matched to the master and then examined interactively for the appearance of new proteins, the loss of normally expressed proteins, and for statistically significant quantitative differences between the control patterns and the "induced" or "ethanol and induced patterns".

Example I

Construction of Expression Vector

A synthetic linker (SEQ ID NO:41) designed to encode the chaperonin binding loop of GroES (EVETKSAGGIVLTGSAAA)(SEQ ID NO:2) was ligated into the EcoRI site of plasmid pJF118EH. Plasmid DNA was prepared from representative colonies arising from transformation of *E. coli* JM 105 with this ligation mixture, and screened for the presence of an AgeI site, which is unique to the introduced linker. Of 10 colonies screened, all contained the site. The plasmids were then screened for orientation of the linker, since it could be incorporated in two directions. The linker was designed so that only one EcoRI site would be regenerated, which in the desired orientation would be attached to the multi-cloning site. Plasmids were digested with EcoRI and EcoRV (present in the tac promoter) and analyzed on a 1.5% gel. The desired orientation, present in 5 of the plasmids, generated a 1,260 base-pair fragment; those in the wrong orientation, with the reconstituted EcoRI site at the downstream side of the inserted linker, generated a fragment of 1,200 basepairs. A representative of the correct orientation was propagated and designated pATP004.

To expand the potential of the vector, the small multi-cloning site of pAF118EH was excised from pATP004 by digesting it with EcoRI and HindIII, and replaced with the EcoRI-HindIII multi-cloning site of pUC19. Of eight colonies screened, seven contained the inserted multi-cloning site. These were further shown to have the expected orientation and the additional restriction sites. A representative colony was designated pATP005.

Example II

Insertion of Genes Into the Expression Vectors

The vectors described above initiate protein synthesis at the ATG codon in the new linker sequence that encodes EVETKSAGGIVLTGSAAA(SEQ ID NO:2). The vector's multi-cloning site follows this linker, and genes are introduced into the cloning sites such that their reading frame matches that of the linker.

The gene encoding mouse Bax was cloned from the pSK-mBax vector and the gene encoding murine Bcl-2 was cloned from cDNA by PCR as described in Materials and Methods. The bax gene was subsequently moved into the EcoRI-BamH1 sites of pATP004 to give the vector pATP011. Genes encoding the BAX homolog Bcl-2 and the *E. Coli* MDH were also recloned into pATP004 by standard methods.

Example III

Expression of the Fusion Protein Comprising BAX-chaperonin Binding Domain

Induction of BAX was compared for three classes of genetic constructs designed to express the BAX gene: 1) without a leader sequence, 2) with the OmpA leader, and 3) with the chaperonin binding domain obtainable from GroES.

Figure 2:
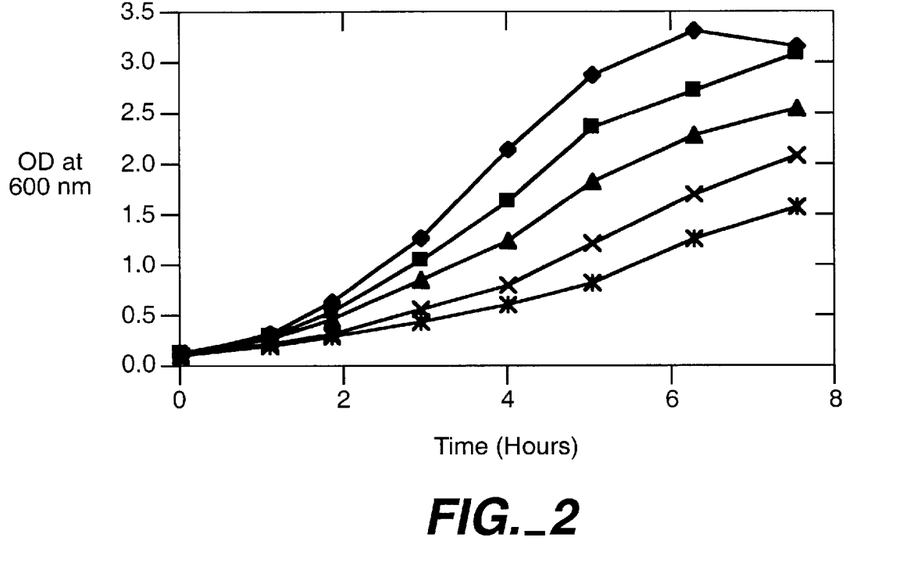
FIG. 2 shows the growth of JM105 in the presence of increasing amount of ethanol: diamonds, no ethanol; squares, 1%; triangles, 2%; X, 3%; *, 4% ethanol in LB media.

The possible effect of the GroES-loop leader sequence on expression of BAX protein was evaluated in cultures that enhance the expression of *E. coli* chaperones in the cell. The rationale was based on the assumption that folding of expressed fusion proteins would be mediated through interaction with the chaperonin GroEL. When grown in the presence of moderate concentrations of ethanol, *E. coli* is known to induce higher levels of chaperones and other stress proteins, Barbarosa, supra. We first evaluated the effect of various concentrations of ethanol on the growth of the host strain, JM 109. A concentration of 2% ethanol (0.44 M) reduced the growth rate approximately 2-fold and was chosen for induction studies (FIG. 2).

Only those transformants containing BAX as a fusion with the chaperonin binding domain obtainable from GroES, showed production of the BAX protein. When those transformants without a leader and not producing BAX were induced, their growth was unaffected. Extracts prepared from these cultures showed patterns of proteins that were identical for the induced and uninduced cultures; there was no evidence of expression of a heterologous protein, either by the appearance of a new band of the expected molecular weight or by alterations in the abundance of *E. coli* host proteins that typically occur on overexpression.

Apparently none of the transformants contained a functional BAX expression system (DNA sequencing analysis of the 5'-end of the genes indicated that the constructs were as expected in that region). In striking contrast, induction of transformants constructed to produce BAX with either of the leader sequences (OmpA or GroES-loop) caused an immediate cessation of growth.

Figure 3:
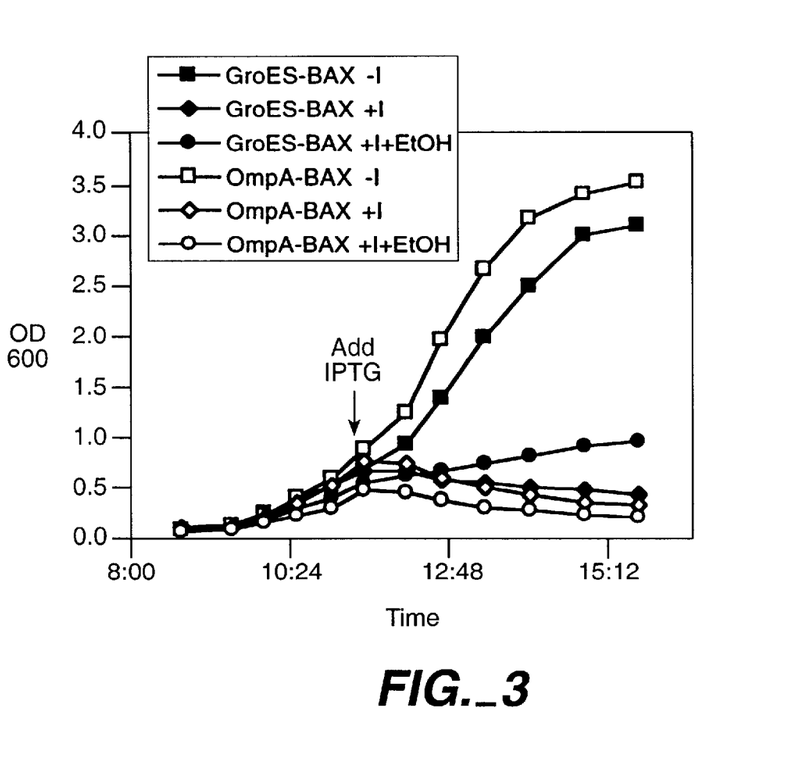
FIG. 3 shows the growth rate of BAX transformants with different leader sequences in the presence and absence of 2% ethanol.
Figure 4:
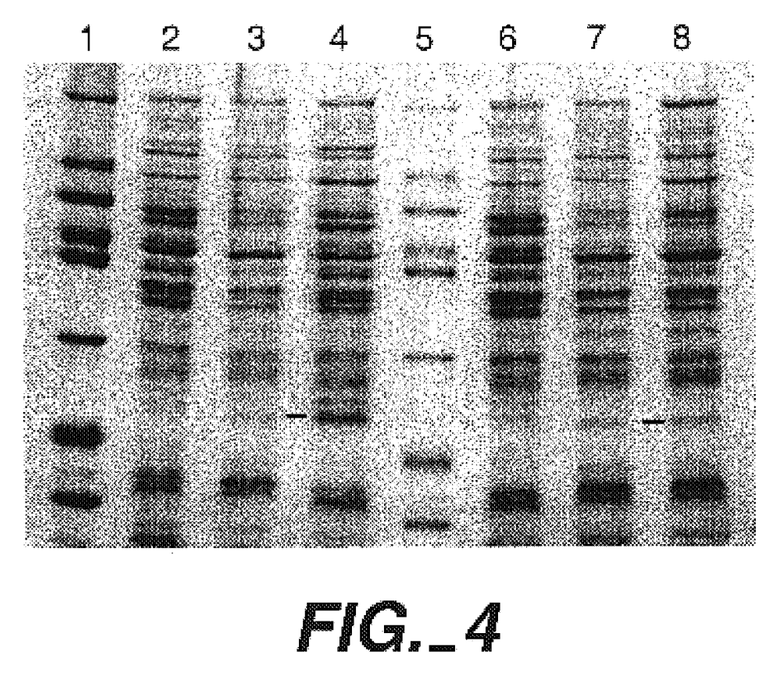
FIG. 4 shows and analysis of proteins present upon induction of the host cells with IPTG and growth in the presence of ethanol. Lanes 1 & 5-MW markers; lanes 2–4-pATP011 (chaperonin binding domain); 6–8-pWS213. (OmpA leader). Bar between lanes 3&4 and 7&8 indicates position of BAX protein on the gel.

Uninduced cells grew normally. In contrast IPTG-induced cells growth dropped immediately following introduction with IPTG (FIG. 3). This apparent strong toxicity of BAX was moderated when cultures were grown in the presence of ethanol, but only in the case of the BAX chimera containing chaperonin binding domain obtainable from GroES (solid circles in FIG. 3). Analyses of the proteins present at the end of this period of induction (FIG. 4) revealed the presence of a new protein of the anticipated molecular weight (indicated by the "bar" in the low molecular weight region (the BAX molecular weight is 21,419 Daltons) of the gel between lanes 3 and 4 and between lanes 7 and 8). The amount of this new protein was quite low in each case except that of having the chaperonin binding domain obtainable from GroES produced in cells grown in the presence of ethanol (FIG. 4). Densitometry of this region of the gel indicated that the presence of ethanol resulted in at least a 15 fold increase in the amount of the BAX produced. Under these conditions inclusion of ethanol induced GroEL production approximately 1.5–1.8 fold.

Due to the presence of other proteins of similar molecular weight, the estimates of relative production of the BAX and GroEL proteins from 1-D gels are inaccurate. Therefore the extracts were separated by 2-dimensional gel electrophoresis (DE). Samples were separated by 2-DE and the resulting protein patterns were analyzed for qualitative and quantitative differences as described in Materials and Methods. The extent of the overexpression of BAX and its enhancement caused by inclusion of ethanol in the culture was found to be greater than that suggested by the 1-dimensional gel analysis. In the absence of IPTG inducer, no protein attributable to BAX was detectable.

The protein pattern analysis indicated that of all the proteins separated on 2DE, only four were overexpressed: GroEL, Hsp70, the fusion of chaperonin binding domain and BAX, and serine hydroxymethyl transferase (Table 3).

TABLE 3

Qualitative analysis of protein expression.

| | condition | avg. density | relative amt |
|---|---|---|---|
| DnaK | control | nos. | 1 |
| | +IPTG (A) | nos. | 0.7 |
| | +IPTG, +EtOH (B) | nos. | 2.1 |
| GroEL | control | nos. | 1 |
| | +IPTG (A) | nos. | 0.85 |
| | +IPTG, +EtOH (B) | nos. | 2.8 |
| SHMT | control | nos. | 1 |
| | +IPTG (A) | nos. | 0.6 |
| | +IPTG, +EtOH (B) | nos. | 1.6 |
| fusion with BAX | control | 0 | 0 |
| | +IPTG (A) | 3089 | — |
| | +IPTG, +EtOH (B) | 45494 | 14.7 rel to –EtOH |

No density above background was detected for the fusion with BAX in the absence of IPTG inducer. The small amount formed when IPTG was present was increased 14.7 fold when cultures were grown with 2% ethanol. Under these conditions, GroEL and Hsp70 were enhanced 3 fold above the amount observed when only IPTG was present.

Various other examples and modifications of the foregoing description and examples will be apparent to a person skilled in the art after reading the disclosure without departing form the spirit and scope of the invention, and it is intended that all such examples or modifications be included within the scope of the appended claims. All publications and patents referenced herein are hereby incorporated in their entirety.

We claim:

1. An expression vector comprising a first nucleic acid encoding an isolated chaperonin binding domain, wherein said chaperonin binding domain consists essentially of an amino acid sequence selected from the group consisting of SEQ ID NO: 2, SEQ ID NO: 3, SEQ ID NO: 4, and SEQ ID NO: 5, and a second nucleic acid encoding a protein, wherein said first nucleic acid and said second nucleic acid are operatively linked to encode a fusion protein.

2. The expression vector of claim 1, wherein the chaperonin binding domain binds to GroEL chaperonin with an affinity of between about $10^{-2}$ and $10^{-8}$ Kd.

3. A host cell containing the expression vector of claim 1.

4. The host cell of claim 3 wherein the host cell is a member of the family Enterobacteriaceae.

5. The host cell of claim 4 wherein the host cell is *E.coli*.

6. A method for producing a protein of interest in a host cell, comprising the steps of:
   a) culturing a host cell comprising a first nucleic acid encoding an isolated chaperonin binding domain consisting essentially of an amino acid sequence selected from the group consisting of SEQ ID NO: 2, SEQ ID NO: 3, SEQ ID NO: 4, and SEQ ID NO: 5, a second nucleic acid encoding said protein of interest, and a third nucleic acid encoding a chaperonin, wherein said chaperonin binding domain binds to said chaperonin, and wherein said first nucleic acid and said second nucleic acid are operatively linked to encode a fusion protein; and
   b) producing the fusion protein comprising said protein of interest.

7. The method of claim 6, further comprising the step of recovering the fusion protein comprising said protein of interest from said host cell.

8. The method of claim 6, where the chaperonin encoded by said third nucleic acid is a chaperonin that is native to said host cell.

9. The method of claim 8, wherein said host cell is cultured under conditions that enhance the levels of said native chaperonin in said host cell.

10. The method of claim 6, wherein said third nucleic acid encoding said chaperonin is heterologous to said host cell.

11. The method of claim 10, wherein said heterologous nucleic acid encoding said chaperonin is under control of an expression signal that produces overexpression of said chaperonin.

12. The method of claim 6, wherein said host cell is a bacterial cell.

13. The method of claim 12, wherein said bacterial cell is a member of the family Enterobacteriaceae.

14. The method of claim 13, wherein said bacterial cell is *E.coli*.

15. The method of claim 6, wherein the chaperonin binding domain binds to GroEL chaperonin with an affinity of between about $10^{-2}$ and $10^{-8}$ Kd.

16. The method of claim 6, wherein said first nucleic acid and said second nucleic acid encoding said fusion protein are separated by a nucleic acid sequence encoding a protease recognition site, wherein said recognition site comprises an enzymatic cleavage site.

17. The method of claim 6, wherein said first nucleic acid and said second nucleic acid encoding said fusion protein are separated by a nucleic acid sequence encoding a chemical cleavage site.

18. The method of claim 6, wherein said protein of interest produced in said host cell is toxic to said host cell.

* * * * *

SEQUENCE LISTING

```
<160> NUMBER OF SEQ ID NOS: 44

<210> SEQ ID NO 1
<211> LENGTH: 54
<212> TYPE: DNA
<213> ORGANISM: Escherichia coli

<400> SEQUENCE: 1
gaagttgaaa ccaaatctgc tggtggtatc gttctgaccg gttctgctgc tgcg        54

<210> SEQ ID NO 2
<211> LENGTH: 18
<212> TYPE: PRT
<213> ORGANISM: Escherichia coli

<400> SEQUENCE: 2

Glu Val Glu Thr Lys Ser Ala Gly Gly Ile Val Leu Thr Gly Ser Ala
 1               5                  10                  15

Ala Ala

<210> SEQ ID NO 3
<211> LENGTH: 19
<212> TYPE: PRT
<213> ORGANISM: Escherichia coli

<400> SEQUENCE: 3

Glu Val Glu Thr Lys Ser Ala Gly Gly Ile Val Leu Thr Gly Ser Ala
 1               5                  10                  15

Ala Ala Lys

<210> SEQ ID NO 4
<211> LENGTH: 19
<212> TYPE: PRT
<213> ORGANISM: Acyrthosiphon pisum

<400> SEQUENCE: 4

Glu Val Glu Ser Lys Ser Ala Gly Gly Ile Val Leu Thr Gly Ser Ala
 1               5                  10                  15

Ala Gly Lys

<210> SEQ ID NO 5
```

```
<211> LENGTH: 19
<212> TYPE: PRT
<213> ORGANISM: Haemophilus ducreyi

<400> SEQUENCE: 5

Glu Val Glu Thr Cys Ser Ala Gly Gly Ile Val Leu Thr Gly Ser Ala
 1               5                  10                  15

Thr Val Lys

<210> SEQ ID NO 6
<211> LENGTH: 19
<212> TYPE: PRT
<213> ORGANISM: Pseudomonas aeruginosa

<400> SEQUENCE: 6

Glu Glu Glu Thr Lys Thr Ala Gly Gly Ile Val Leu Pro Gly Ser Ala
 1               5                  10                  15

Ala Glu Lys

<210> SEQ ID NO 7
<211> LENGTH: 19
<212> TYPE: PRT
<213> ORGANISM: Allochromatium vinosum

<400> SEQUENCE: 7

Glu Glu Glu Arg Leu Ser Ala Gly Gly Ile Val Ile Pro Asp Ser Ala
 1               5                  10                  15

Thr Glu Lys

<210> SEQ ID NO 8
<211> LENGTH: 19
<212> TYPE: PRT
<213> ORGANISM: Coxiella burnetii

<400> SEQUENCE: 8

Glu Glu Glu Arg Thr Ser Ala Gly Gly Ile Val Ile Pro Asp Ser Ala
 1               5                  10                  15

Ala Glu Lys

<210> SEQ ID NO 9
<211> LENGTH: 19
<212> TYPE: PRT
<213> ORGANISM: Legionella micdadei

<400> SEQUENCE: 9

Glu Glu Glu Arg Thr Thr Ala Gly Gly Ile Val Ile Pro Asp Ser Ala
 1               5                  10                  15

Thr Glu Lys

<210> SEQ ID NO 10
<211> LENGTH: 19
<212> TYPE: PRT
<213> ORGANISM: Sinorhizobium meliloti

<400> SEQUENCE: 10

Glu Ser Glu Glu Lys Thr Lys Gly Gly Ile Ile Ile Pro Asp Thr Ala
 1               5                  10                  15

Lys Glu Lys

<210> SEQ ID NO 11
<211> LENGTH: 19
```

-continued

```
<212> TYPE: PRT
<213> ORGANISM: Legionella pneumophila

<400> SEQUENCE: 11

Glu Glu Glu Arg Thr Thr Ala Gly Gly Ile Val Ile Pro Asp Ser Ala
1 5 10 15

Thr Glu Lys

<210> SEQ ID NO 12
<211> LENGTH: 19
<212> TYPE: PRT
<213> ORGANISM: Brucella abortus

<400> SEQUENCE: 12

Glu Ser Glu Ala Lys Thr Ala Gly Gly Ile Ile Ile Pro Asp Thr Ala
1 5 10 15

Lys Glu Lys

<210> SEQ ID NO 13
<211> LENGTH: 19
<212> TYPE: PRT
<213> ORGANISM: Bradyrhizobium japonicum

<400> SEQUENCE: 13

Asp Ala Glu Glu Lys Thr Ala Gly Gly Ile Ile Ile Pro Asp Thr Val
1 5 10 15

Lys Glu Lys

<210> SEQ ID NO 14
<211> LENGTH: 19
<212> TYPE: PRT
<213> ORGANISM: Agrobacterium tumefaciens

<400> SEQUENCE: 14

Glu Ser Glu Ala Lys Thr Lys Gly Gly Ile Ile Ile Pro Asp Thr Ala
1 5 10 15

Lys Glu Lys

<210> SEQ ID NO 15
<211> LENGTH: 19
<212> TYPE: PRT
<213> ORGANISM: Clostridium acetobutylieum

<400> SEQUENCE: 15

Glu Ala Glu Glu Thr Thr Lys Ser Gly Ile Val Leu Pro Ser Ser Ala
1 5 10 15

Lys Glu Lys

<210> SEQ ID NO 16
<211> LENGTH: 19
<212> TYPE: PRT
<213> ORGANISM: Amoeba proteus

<400> SEQUENCE: 16

Glu Glu Glu Arg Thr Thr Ala Gly Trp Ile Val Ile Pro Asp Ser Ala
1 5 10 15

Thr Glu Lys

<210> SEQ ID NO 17
<211> LENGTH: 19
<212> TYPE: PRT
```

```
<213> ORGANISM: Sinorhizobium meliloti

<400> SEQUENCE: 17

Glu Ser Glu Glu Lys Thr Lys Gly Gly Ile Ile Ile Pro Asp Thr Ala
1               5                   10                  15

Lys Glu Lys

<210> SEQ ID NO 18
<211> LENGTH: 19
<212> TYPE: PRT
<213> ORGANISM: Lactococcus lactic

<400> SEQUENCE: 18

Glu Glu Glu Glu Lys Ser Met Gly Gly Ile Val Leu Thr Ser Ala Ser
1               5                   10                  15

Gln Glu Lys

<210> SEQ ID NO 19
<211> LENGTH: 19
<212> TYPE: PRT
<213> ORGANISM: Streptomyces albus

<400> SEQUENCE: 19

Asp Ala Glu Gln Thr Thr Ala Ser Gly Leu Val Ile Pro Asp Thr Ala
1               5                   10                  15

Lys Glu Lys

<210> SEQ ID NO 20
<211> LENGTH: 19
<212> TYPE: PRT
<213> ORGANISM: Thermoactinomyces sp.

<400> SEQUENCE: 20

Glu Thr Glu Glu Lys Thr Ala Ser Gly Ile Val Leu Pro Asp Thr Ala
1               5                   10                  15

Lys Glu Lys

<210> SEQ ID NO 21
<211> LENGTH: 19
<212> TYPE: PRT
<213> ORGANISM: Bacillus subtilis

<400> SEQUENCE: 21

Glu Ser Glu Glu Lys Thr Ala Ser Gly Ile Val Leu Pro Asp Ser Ala
1               5                   10                  15

Lys Glu Lys

<210> SEQ ID NO 22
<211> LENGTH: 19
<212> TYPE: PRT
<213> ORGANISM: Bacillus stearothermophilus

<400> SEQUENCE: 22

Glu Thr Glu Glu Lys Thr Ala Ser Gly Ile Val Leu Pro Asp Thr Ala
1               5                   10                  15

Lys Glu Lys

<210> SEQ ID NO 23
<211> LENGTH: 19
<212> TYPE: PRT
<213> ORGANISM: Mycobacterium tuberculosis
```

<400> SEQUENCE: 23

Glu Ala Glu Thr Thr Thr Ala Ser Gly Leu Val Ile Pro Asp Thr Ala
 1               5                  10                  15

Lys Glu Lys

<210> SEQ ID NO 24
<211> LENGTH: 19
<212> TYPE: PRT
<213> ORGANISM: Bradyrhizobium japonicum

<400> SEQUENCE: 24

Asp Ala Glu Glu Lys Thr Ala Gly Gly Ile Ile Ile Pro Asp Thr Ala
 1               5                  10                  15

Lys Glu Lys

<210> SEQ ID NO 25
<211> LENGTH: 19
<212> TYPE: PRT
<213> ORGANISM: Staphylococcus aureus

<400> SEQUENCE: 25

Glu Gln Glu Gln Thr Thr Lys Ser Gly Ile Val Leu Thr Asp Ser Ala
 1               5                  10                  15

Lys Glu Lys

<210> SEQ ID NO 26
<211> LENGTH: 19
<212> TYPE: PRT
<213> ORGANISM: Mycobacterium bovis

<400> SEQUENCE: 26

Glu Ala Glu Thr Thr Thr Ala Ser Gly Leu Val Ile Pro Asp Thr Ala
 1               5                  10                  15

Lys Glu Lys

<210> SEQ ID NO 27
<211> LENGTH: 19
<212> TYPE: PRT
<213> ORGANISM: Mycobacterium lepvae

<400> SEQUENCE: 27

Glu Ala Glu Thr Met Thr Pro Ser Gly Leu Val Ile Pro Glu Asn Ala
 1               5                  10                  15

Lys Glu Lys

<210> SEQ ID NO 28
<211> LENGTH: 19
<212> TYPE: PRT
<213> ORGANISM: Clostridium perfringens

<400> SEQUENCE: 28

Glu Ala Glu Glu Thr Thr Lys Ser Gly Ile Ile Val Thr Gly Thr Ala
 1               5                  10                  15

Lys Glu Arg

<210> SEQ ID NO 29
<211> LENGTH: 19
<212> TYPE: PRT
<213> ORGANISM: Synechococcus PCC7942

```
<400> SEQUENCE: 29

Glu Ala Glu Glu Lys Thr Ala Gly Gly Ile Ile Leu Pro Asp Asn Ala
 1               5                  10                  15

Lys Glu Lys

<210> SEQ ID NO 30
<211> LENGTH: 19
<212> TYPE: PRT
<213> ORGANISM: Synechococcus PCC6301

<400> SEQUENCE: 30

Glu Ala Glu Glu Lys Thr Ala Gly Gly Ile Ile Leu Pro Asp Asn Ala
 1               5                  10                  15

Lys Glu Lys

<210> SEQ ID NO 31
<211> LENGTH: 19
<212> TYPE: PRT
<213> ORGANISM: Synechocystis PCC6803

<400> SEQUENCE: 31

Pro Ala Glu Glu Lys Thr Ala Gly Gly Ile Leu Leu Pro Asp Asn Ala
 1               5                  10                  15

Lys Glu Lys

<210> SEQ ID NO 32
<211> LENGTH: 19
<212> TYPE: PRT
<213> ORGANISM: Chlamydophila pheumoniae

<400> SEQUENCE: 32

Glu Glu Glu Ala Thr Ala Arg Gly Gly Ile Ile Leu Pro Asp Thr Ala
 1               5                  10                  15

Lys Lys Lys

<210> SEQ ID NO 33
<211> LENGTH: 19
<212> TYPE: PRT
<213> ORGANISM: Leptospiya interrogans

<400> SEQUENCE: 33

Gln Glu Ala Glu Lys Ile Gly Ser Ile Phe Val Pro Asp Thr Ala
 1               5                  10                  15

Lys Glu Lys

<210> SEQ ID NO 34
<211> LENGTH: 19
<212> TYPE: PRT
<213> ORGANISM: Chlamydophila psittaci

<400> SEQUENCE: 34

Glu Glu Asp Ser Thr Ala Arg Gly Gly Ile Ile Leu Pro Asp Thr Ala
 1               5                  10                  15

Lys Lys Lys

<210> SEQ ID NO 35
<211> LENGTH: 19
<212> TYPE: PRT
<213> ORGANISM: Chlamydia trachomatis

<400> SEQUENCE: 35
```

Glu Glu Ala Ser Thr Ala Arg Gly Gly Ile Ile Leu Pro Asp Thr Ala
1               5                   10                  15

Lys Lys Lys

<210> SEQ ID NO 36
<211> LENGTH: 19
<212> TYPE: PRT
<213> ORGANISM: Rattus norregiens

<400> SEQUENCE: 36

Ala Ala Glu Thr Val Thr Lys Gly Gly Ile Met Leu Pro Glu Lys Ser
1               5                   10                  15

Gln Gly Lys

<210> SEQ ID NO 37
<211> LENGTH: 19
<212> TYPE: PRT
<213> ORGANISM: Bos taurus

<400> SEQUENCE: 37

Ala Ala Glu Thr Val Thr Lys Gly Gly Ile Met Leu Pro Glu Lys Ser
1               5                   10                  15

Gln Gly Lys

<210> SEQ ID NO 38
<211> LENGTH: 18
<212> TYPE: PRT
<213> ORGANISM: Orienta tsutsugamushi

<400> SEQUENCE: 38

Gln Asn Asp Glu Ala His Gly Lys Ile Leu Ile Pro Asp Thr Ala Lys
1               5                   10                  15

Glu Lys

<210> SEQ ID NO 39
<211> LENGTH: 19
<212> TYPE: PRT
<213> ORGANISM: Spirillospora sp.

<400> SEQUENCE: 39

Glu Val Glu Asn Lys Thr Ser Gly Gly Leu Leu Leu Ala Glu Ser Ser
1               5                   10                  15

Lys Glu Lys

<210> SEQ ID NO 40
<211> LENGTH: 18
<212> TYPE: PRT
<213> ORGANISM: Arabidopsis thaliana

<400> SEQUENCE: 40

Ile Gln Pro Ala Lys Thr Glu Ser Gly Ile Leu Leu Pro Glu Lys Ser
1               5                   10                  15

Ser Lys

<210> SEQ ID NO 41
<211> LENGTH: 54
<212> TYPE: DNA
<213> ORGANISM: Artificial Sequence
<220> FEATURE:
<223> OTHER INFORMATION: oligonucleotide

```
<400> SEQUENCE: 41
gaagttgaaa ccaaatctgc tggtggtatc gttctgaccg gttctgctgc tgcg          54

<210> SEQ ID NO 42
<211> LENGTH: 61
<212> TYPE: DNA
<213> ORGANISM: Artificial Sequence
<220> FEATURE:
<223> OTHER INFORMATION: oligonucleotide

<400> SEQUENCE: 42
aattcgcagc agcagaaccg gtcagaacga taccaccagc agatttggtt tcaacttcca    60
t                                                                    61

<210> SEQ ID NO 43
<211> LENGTH: 20
<212> TYPE: PRT
<213> ORGANISM: Artificial Sequence
<220> FEATURE:
<223> OTHER INFORMATION: linker

<400> SEQUENCE: 43

Met Glu Val Glu Thr Lys Ser Ala Gly Gly Ile Val Leu Thr Gly Ser
 1               5                  10                  15

Ala Ala Ala Asn
            20

<210> SEQ ID NO 44
<211> LENGTH: 61
<212> TYPE: DNA
<213> ORGANISM: Artificial Sequence
<220> FEATURE:
<223> OTHER INFORMATION: linker

<400> SEQUENCE: 44
aattatggaa gttgaaacca atctgctgg tggtatcgtt ctgaccggtt ctgctgctgc     60
g                                                                    61
```